United States Patent
Sughrue et al.

(10) Patent No.: US 12,308,119 B2
(45) Date of Patent: May 20, 2025

(54) MAPPING BRAIN DATA TO BEHAVIOR

(71) Applicant: Omniscient Neurotechnology Pty Limited, Sydney (AU)

(72) Inventors: Michael Edward Sughrue, Sydney (AU); Stephane Philippe Doyen, Glebe (AU)

(73) Assignee: Omniscient Neurotechnology Pty Limited, Sydney (AU)

( * ) Notice: Subject to any disclaimer, the term of this patent is extended or adjusted under 35 U.S.C. 154(b) by 0 days.

(21) Appl. No.: 17/499,845

(22) Filed: Oct. 12, 2021

(65) Prior Publication Data
US 2023/0112160 A1    Apr. 13, 2023

(51) Int. Cl.
| | | |
|---|---|---|
| G06N 20/00 | (2019.01) | |
| G06N 5/01 | (2023.01) | |
| G06N 20/20 | (2019.01) | |
| G16H 30/40 | (2018.01) | |
| G16H 50/20 | (2018.01) | |
| G16H 50/70 | (2018.01) | |

(52) U.S. Cl.
CPC .......... *G16H 50/20* (2018.01); *G06N 5/01* (2023.01); *G06N 20/20* (2019.01); *G16H 30/40* (2018.01); *G16H 50/70* (2018.01)

(58) Field of Classification Search
CPC ....... A61B 5/165; A61B 5/0042; A61B 5/369; A61B 5/4064; A61B 5/16
See application file for complete search history.

(56) References Cited

U.S. PATENT DOCUMENTS

| | | | |
|---|---|---|---|
| 11,151,456 B1* | 10/2021 | Sughrue | G06N 3/0454 |
| 11,581,082 B2* | 2/2023 | Sughrue | G16H 10/20 |
| 2008/0086272 A1* | 4/2008 | Fillet | G16B 20/00 |
| | | | 702/19 |
| 2013/0261490 A1* | 10/2013 | Truccolo | A61B 5/374 |
| | | | 600/544 |
| 2014/0279746 A1* | 9/2014 | De Bruin | A61B 5/7267 |
| | | | 706/12 |
| 2014/0344193 A1* | 11/2014 | Bilenko | G06N 20/00 |
| | | | 706/12 |

(Continued)

FOREIGN PATENT DOCUMENTS

KR    10-2021-0059272    5/2021

OTHER PUBLICATIONS

Defination of Vector—Merriam-Websters https://www.merriam-webster.com/dictionary/vector.*

(Continued)

*Primary Examiner* — David R Vincent
(74) *Attorney, Agent, or Firm* — Fish & Richardson P.C.

(57) ABSTRACT

Methods, systems, and apparatus, including computer programs encoded on computer storage media, for mapping aspects of a connectivity matrix to a specific quantified behavioral expression. One of the methods includes: obtaining a set of brain data captured by one or more sensors, the set of brain data characterizing brain activity patterns of one or more patients; determining, using a trained decision tree model, a parcel of the brain associated with a behavioral measurement based at least in part on the brain data, the trained decision tree model trained using a set of training brain data characterized with a degree of the behavior; and taking an action based on the determination.

20 Claims, 9 Drawing Sheets

(56) References Cited

U.S. PATENT DOCUMENTS

| | | | | |
|---|---|---|---|---|
| 2017/0039045 | A1* | 2/2017 | Abrahami | A61P 3/04 |
| 2017/0343634 | A1* | 11/2017 | Lencz | A61B 5/055 |
| 2018/0085040 | A1* | 3/2018 | Ferber | A61B 5/7278 |
| 2018/0365272 | A1* | 12/2018 | Sastry | G06F 16/2246 |
| 2020/0117580 | A1* | 4/2020 | Lekivetz | G06F 11/3684 |
| 2020/0337625 | A1* | 10/2020 | Aimone | G16H 40/67 |
| 2020/0410890 | A1 | 12/2020 | Yamada et al. | |
| 2021/0041953 | A1 | 2/2021 | Poltorak | |
| 2021/0107501 | A1* | 4/2021 | Monteil | B60W 40/09 |
| 2021/0169417 | A1* | 6/2021 | Burton | A61B 5/4857 |
| 2022/0208339 | A1* | 6/2022 | Neumann | G06F 16/242 |
| 2023/0107263 | A1* | 4/2023 | Kashiwagi | G06F 18/211 |
| | | | | 600/410 |

OTHER PUBLICATIONS

Han et al., "Classification and Biomarker Identification In Autism Using Conjunctive Clause Evolutionary Algorithm," Nov. 12, 2020, retrieved on Nov. 28, 2022, retrieved from URL :<https://www.medrxiv.org/content/ 10.11. Jan. 2020. 11.09.202020227843v 1>, 17 pages.

International Search Report and Written Opinion in International Appln. No. PCT/AU2022/051095, mailed on Dec. 8, 2022, 9 pages.

Silva, "Contributions to the Study of Autism Spectrum Brain Connectivity," May 21, 2021, retrieved on Nov. 28, 2022, retrieved from URL :<https://www.ehu.eus/ccwintco/index.php?title=Archivo:ThesisMoises210521.pdf>, 156 pages.

International Preliminary Report on Patentability in International Appln. No. PCT/AU2022/051095, mailed on Apr. 25, 2024, 7 pages.

* cited by examiner

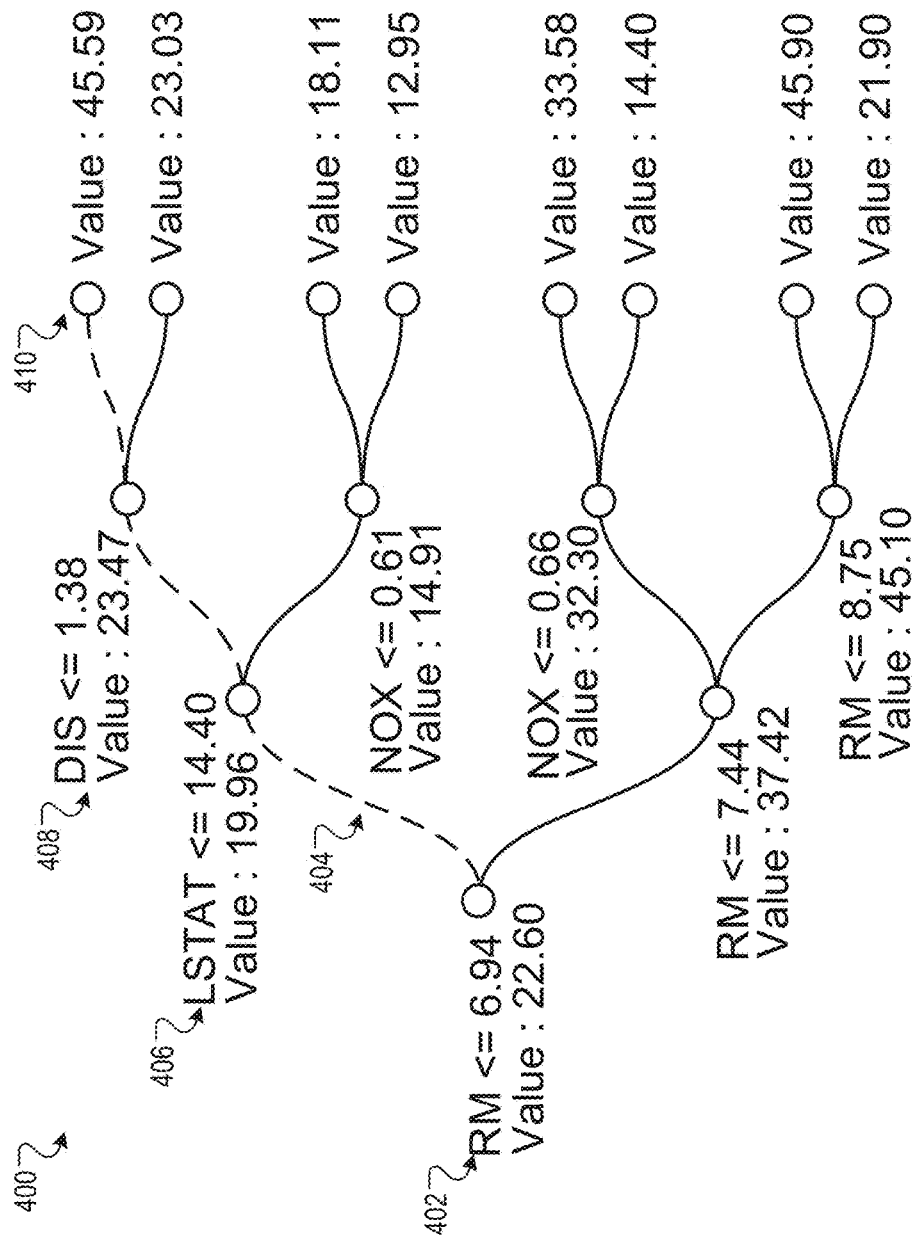

| target | feature | weight | value | feature_0 | feature_1 | abs_weight | rank_weight | prod | abs_prod | rank_prod |
|---|---|---|---|---|---|---|---|---|---|---|
| 1 | R_47l-R_AAIC | 0.77281 | 0.351181 | R_47l | R_AAIC | 0.77281 | 0 | 0.271397 | 0.271397 | 0 |
| 1 | R_3b-R_TP0J1 | 0.574417 | 0.417938 | R_3b | R_TP0J1 | 0.574417 | 1 | 0.240071 | 0.240071 | 1 |
| 1 | R-6a-R_p24 | -0.454656 | -0.348543 | R_6a | R_p24 | 0.454656 | 3 | 0.158467 | 0.158467 | 2 |
| 1 | R-6d-L_IPS1 | 0.290432 | 0.45443 | R_6d | L_IPS1 | 0.290432 | 6 | 0.131985 | 0.131985 | 3 |

FIG. 5

MAPPING BRAIN DATA TO BEHAVIOR

TECHNICAL FIELD

The present disclosure generally relates to using machine learning on medical imaging data.

BACKGROUND

Medical imaging includes the technique and process of creating visual representations of the interior of a body for clinical analysis and medical intervention, as well as visual representation of the function of some organs or tissues (physiology). Medical imaging seeks to reveal internal structures hidden by the skin and bones, as well as to diagnose and treat disease. Medical imaging also establishes a database of normal anatomy and physiology. Machine learning can be used as a tool to help identify normal and abnormal traits.

SUMMARY

This specification describes technologies for using machine learning on brain data captured by one or more sensors, where the brain data characterizes brain activity patterns of one or more patients, to identify particular activity pattern(s) that are characteristic of a degree of a behavior, trait, or symptom, and take an action based on identification of such pattern(s). For example, the machine learning process may be used to identify one or more symptoms of a disease or disorder that are likely to impact measurably the quality of life of a subject, enabling the design of an effective treatment plan.

Connectivity matrices are rich data sources which can provide valuable insights on what specific brain activity underlies a symptom or a behavioral expression. In one implementation a series of analytical steps and machine learning techniques provide a mapping of aspects of a connectivity matrix to a specific quantified behavioral expression. For instance, implementations can provide insights as to what specific part of the brain is responsible for Schizophrenic patients hearing voices.

In general, one innovative aspect of the subject matter described in this specification can be embodied in methods that include the actions of: obtaining a set of brain data captured by one or more sensors, the set of brain data characterizing brain activity patterns of one or more patients; determining, using a trained decision tree model, a parcel of the brain associated with a behavioral measurement based at least in part on the brain data, the trained decision tree model trained using a set of training brain data characterized with a degree of the behavior; and taking an action based on the determination. In general, another innovative aspect of the subject matter described in this specification can be embodied in methods that include the actions of: obtaining a set of brain data captured by one or more sensors, the set of brain data characterizing brain activity patterns of one or more patients; determining, using a trained decision model, a parcel of the brain associated with a behavioral measurement based at least in part on the brain data, the trained decision model trained using a set of training brain data characterized with a degree of the behavior; and taking an action based on the determination. The decision model can be selected from one of a) a tree model and b) a logistic regression model Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination. In particular, one embodiment includes all the following features in combination. The behavioral measurement can be a behavior expression metric scored on a standardized scale. The trained decision tree model can be an ensemble tree model. The brain data can be selected from at least one of, Magnetoencephalograph (MEG), electroencephalograph (EEG), magnetic resonance imaging (MM), diffusion tensor imaging (DTI), near-infrared spectroscopy (NIRS), or functional MRI imaging (fMRI). The brain data can be resting state fMRI data.

Determining a parcel of the brain associated with a behavioral measurement can include: performing cross-validation of the trained decision tree model; and applying a weight to each combination of brain activity pattern and degree of behavior, the weight indicative of the importance of that brain activity pattern for predicting the degree of behavior or presence of symptom. Performing cross-validation can include: a) constructing a plurality of iterations of the brain data, the iterations divided into a plurality of folds; b) for each iteration of the plurality of iterations: i) selecting a fold as a test fold; ii) training a decision tree on the remainder of the folds to produce a trained decision tree; iii) determining a predicted outcome for the test fold using the trained decision tree and iv) determining a test outcome based on a comparison of a predicted outcome for the test fold and an actual outcome for the test fold, wherein a different test fold is selected for each iteration; c) aggregating predicted outcomes based at least in part on the test outcomes; and d) using the aggregated predicted outcomes to determine a degree of a behavior based at least in part on new brain data.

Cross validation in the training phase of the model is a means to ensure good fit of the model but not a requirement of this method. Good fit can be achieved without cross-validation. Furthermore, other models that are not tree based could be applied. The underlying principle is looking at feature importance of a model that was fit using the connectome.

The method can further include, for each patient of the one more patients, ranking each combination of brain activity data and degree of a behavior based at least in part on the weight indicative of the strength of cross validation. The method can further include aggregating the ranking for all patients to provide an indication of a strength of the cross-validation.

Determining a parcel of the brain associated with a behavioral measurement can include: performing hyperparameter tuning; evaluating combinations of parameters with cross-validation; selecting a combination of parameters that perform above a specified threshold; applying this set of parameters to a full dataset; and applying a weight to each combination of brain activity pattern, the weight indicative of the importance of that brain activity pattern for predicting the degree of behavior or presence of symptom.

The behavior can be a symptom of a disease. The behavior can be a response to a treatment. The behavior can be a trait. The method can include processing the brain data to produce connectivity matrix data and determining a degree of a behavior can include determining a degree of a behavior based at least in part on the connectivity matrix data.

The subject matter described in this specification can be implemented in particular embodiments so as to realize one or more of the following advantages. A symptom or behavior expression can be identified (and in some implementations quantified) from brain data (e.g., connectomic brain data) using machine learning. In particular, parcels (e.g. volumes or regions) of the brain associated with symptoms or behaviors can be identified from small samples and high dimensional data, providing insights on complex relations and magnitudes and directionality of predictors. The embodiments described allow objective measurement of the areas of the brain associated with a particular symptom or behavior. Given the nature of the task, it would not be practical to do without using automated methods, e.g., machine learning models such as a decision tree model or an ensemble decision tree model. Machine learning offers greater consistency and speed and is generally considered to be less biased.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIG. 4 is a schematic diagram of an example of machine learning using boosted trees.

FIG. 5 is a schematic diagram of an example decision table for a subject.

Like reference numbers and designations in the various drawings indicate like elements.

DETAILED DESCRIPTION

This specification describes a system that can map connectomic data (e.g., using machine learning techniques such as a tree based model) to a quantified behavioral expression (e.g., a quantified symptom or trait). For example, in the context of schizophrenia, a symptom or trait could be how much a subject is hearing voices ranked on a standardized scale.

Figure 1A:
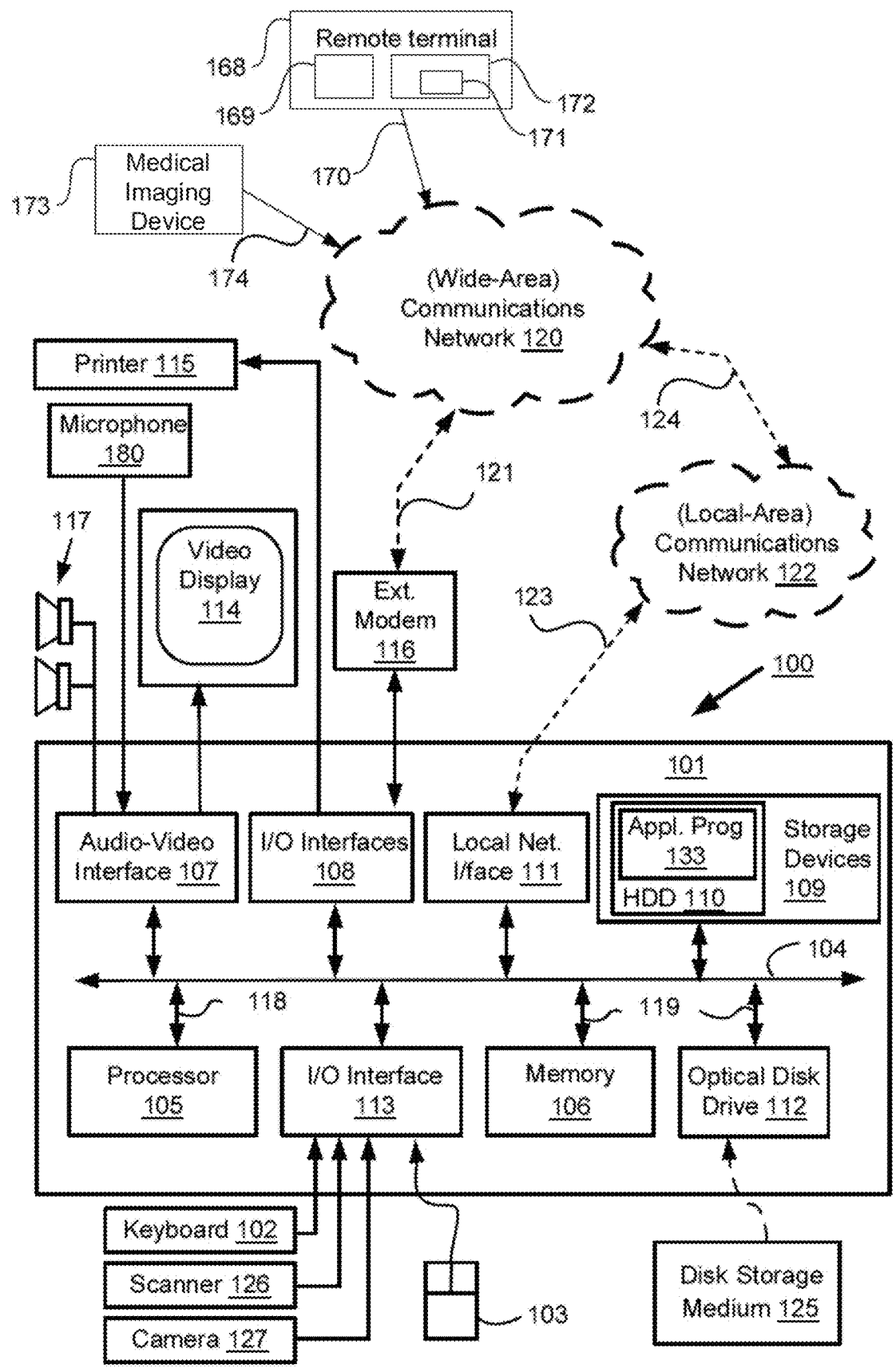
FIG. 1A and FIG. 1B are block diagrams that illustrate an example computer system for use in processing medical images.
Figure 1B:
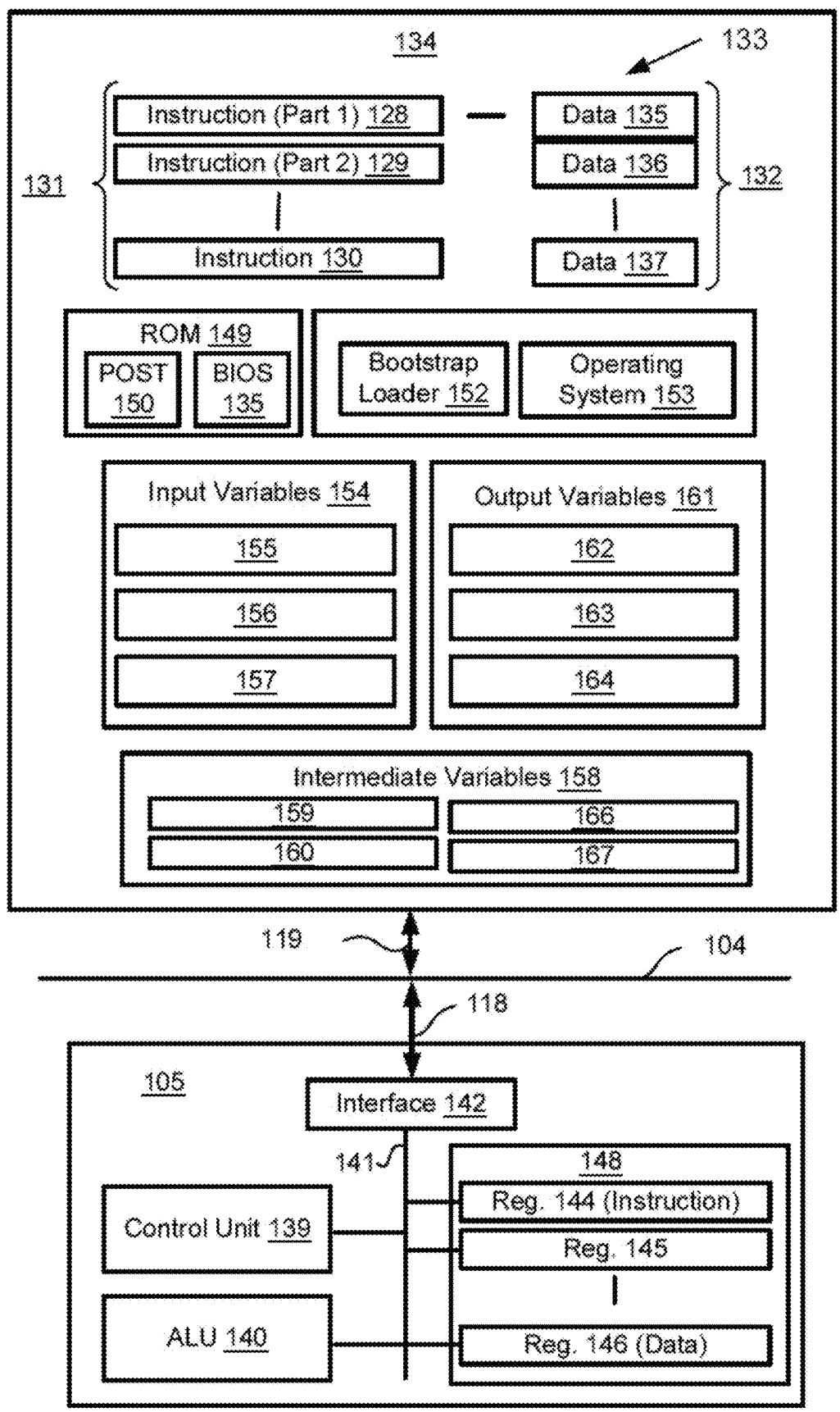

FIGS. 1A and 1B are block diagrams of a computer system 100 upon which one can practice arrangements described in this specification. The following description is directed primarily to a computer server module 101. However, the description applies equally or equivalently to one or more remote terminals 168.

As seen in FIG. 1A, the computer system 100 includes: the server computer module 101; input devices such as a keyboard 102, a pointer device 103 (e.g., a mouse), a scanner 126, a camera 127, and a microphone 180; and output devices including a printer 115, a display device 114 and loudspeakers 117. An external Modulator-Demodulator (Modem) transceiver device 116 may be used by the computer server module 101 for communicating to and from the remote terminal 168 over a computer communications network 120 via a connection 121 and a connection 170. The aforementioned communication can take place between the remote terminal 168 and "the cloud" which in the present description comprises at least the one server module 101. The remote terminal 168 typically has input and output devices (not shown) which are similar to those described in regard to the server module 101. The communications network 120 may be a wide-area network (WAN), such as the Internet, a cellular telecommunications network, or a private WAN. Where the connection 121 is a telephone line, the modem 116 may be a traditional "dial-up" modem. Alternatively, where the connection 121 is a high capacity (e.g., cable) connection, the modem 116 may be a broadband modem. A wireless modem may also be used for wireless connection to the communications network 120.

The computer server module 101 typically includes at least one processor unit 105, and a memory unit 106. For example, the memory unit 106 may have semiconductor random access memory (RAM) and semiconductor read only memory (ROM). The remote terminal 168 typically includes as least one processor 169 and a memory 172. The computer server module 101 also includes a number of input/output (I/O) interfaces including: an audio-video interface 107 that couples to the video display 114, loudspeakers 117 and microphone 180; an I/O interface 113 that couples to the keyboard 102, mouse 103, scanner 126, camera 127 and optionally a joystick or other human interface device (not illustrated); and an interface 108 for the external modem 116 and printer 115. In some implementations, the modem 116 may be incorporated within the computer module 101, for example within the interface 108. The computer module 101 also has a local network interface 111, which permits coupling of the computer system 100 via a connection 123 to a local-area communications network 122, known as a Local Area Network (LAN). As illustrated in FIG. 1A, the local communications network 122 may also couple to the wide network 120 via a connection 124, which would typically include a so-called "firewall" device or device of similar functionality. The local network interface 111 may include an Ethernet circuit card, a Bluetooth® wireless arrangement or an IEEE 802.11 wireless arrangement; however, numerous other types of interfaces may be practiced for the interface 111.

The I/O interfaces 108 and 113 may afford either or both of serial or parallel connectivity; the former may be implemented according to the Universal Serial Bus (USB) standards and having corresponding USB connectors (not illustrated). Storage memory devices 109 are provided and typically include a hard disk drive (HDD) 110. Other storage devices such as a floppy disk drive and a magnetic tape drive (not illustrated) may also be used. An optical disk drive 112 is typically provided to act as a non-volatile source of data. Portable memory devices, such optical disks (e.g., CD-ROM, DVD, Blu-ray Disc™), USB-RAM, portable, external hard drives, and floppy disks, for example, may be used as appropriate sources of data to the system 100.

The components 105 to 113 of the computer module 101 typically communicate via an interconnected bus 104 and in a manner that results in a conventional mode of operation of the computer system 100 known to those in the relevant art. For example, the processor 105 is coupled to the system bus 104 using a connection 118. Likewise, the memory 106 and optical disk drive 112 are coupled to the system bus 104 by connections 119.

The techniques described in this specification may be implemented using the computer system 100, e.g., may be implemented as one or more software application programs 133 executable within the computer system 100. In some implementations, the one or more software application programs 133 execute on the computer server module 101 (the remote terminal 168 may also perform processing jointly with the computer server module 101), and a browser 171 executes on the processor 169 in the remote terminal, thereby enabling a user of the remote terminal 168 to access the software application programs 133 executing on the server 101 (which is often referred to as "the cloud") using the browser 171. In particular, the techniques described in this specification may be effected by instructions 131 (see FIG. 1B) in the software 133 that are carried out within the computer system 100. The software instructions 131 may be formed as one or more code modules, each for performing one or more particular tasks. The software may also be divided into two separate parts, in which a first part and the corresponding code modules performs the described techniques and a second part and the corresponding code modules manage a user interface between the first part and the user.

The software may be stored in a computer readable medium, including the storage devices described below, for example. The software is loaded into the computer system 100 from the computer readable medium, and then executed by the computer system 100. A computer readable medium having such software or computer program recorded on the computer readable medium is a computer program product. Software modules for that execute techniques described in this specification may also be distributed using a Web browser.

The software 133 is typically stored in the HDD 110 or the memory 106 (and possibly at least to some extent in the memory 172 of the remote terminal 168). The software is loaded into the computer system 100 from a computer readable medium, and executed by the computer system 100. Thus, for example, the software 133, which can include one or more programs, may be stored on an optically readable disk storage medium (e.g., CD-ROM) 125 that is read by the optical disk drive 112. A computer readable medium having such software or computer program recorded on it is a computer program product.

In some instances, the application programs 133 may be supplied to the user encoded on one or more CD-ROMs 125 and read via the corresponding drive 112, or alternatively may be read by the user from the networks 120 or 122. Still further, the software can also be loaded into the computer system 100 from other computer readable media. Computer readable storage media refers to any non-transitory tangible storage medium that provides recorded instructions and/or data to the computer system 100 for execution and/or processing. Examples of such storage media include floppy disks, magnetic tape, CD-ROM, DVD, Blu-ray™ Disc, a hard disk drive, a ROM or integrated circuit, USB memory, a magneto-optical disk, or a computer readable card such as a PCMCIA card and the like, whether or not such devices are internal or external of the computer module 101. Examples of transitory or non-tangible computer readable transmission media that may also participate in the provision of software, application programs, instructions and/or data to the computer module 101 include radio or infra-red transmission channels as well as a network connection to another computer or networked device, and the Internet or Intranets including e-mail transmissions and information recorded on Websites and the like.

The second part of the application programs 133 and the corresponding code modules mentioned above may be executed to implement one or more graphical user interfaces (GUIs) to be rendered or otherwise represented upon the display 114. For example, through manipulation of the keyboard 102 and the mouse 103, a user of the computer system 100 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 117 and user voice commands input via the microphone 180.

FIG. 1B is a detailed schematic block diagram of the processor 105 and a "memory" 134. The memory 134 represents a logical aggregation of all the memory modules (including the HDD 109 and semiconductor memory 106) that can be accessed by the computer module 101 in FIG. 1A.

When the computer module 101 is initially powered up, a power-on self-test (POST) program 150 can execute. The POST program 150 can be stored in a ROM 149 of the semiconductor memory 106 of FIG. 1A. A hardware device such as the ROM 149 storing software is sometimes referred to as firmware. The POST program 150 examines hardware within the computer module 101 to ensure proper functioning and typically checks the processor 105, the memory 134 (109, 106), and a basic input-output systems software (BIOS) module 151, also typically stored in the ROM 149, for correct operation. Once the POST program 150 has run successfully, the BIOS 151 can activate the hard disk drive 110 of FIG. 1A. Activation of the hard disk drive 110 causes a bootstrap loader program 152 that is resident on the hard disk drive 110 to execute via the processor 105. This loads an operating system 153 into the RAM memory 106, upon which the operating system 153 commences operation. The operating system 153 is a system level application, executable by the processor 105, to fulfil various high-level functions, including processor management, memory management, device management, storage management, software application interface, and generic user interface.

The operating system 153 manages the memory 134 (109, 106) to ensure that each process or application running on the computer module 101 has sufficient memory in which to execute without colliding with memory allocated to another process. Furthermore, the different types of memory available in the system 100 of FIG. 1A must be used properly so that each process can run effectively. Accordingly, the aggregated memory 134 is not intended to illustrate how particular segments of memory are allocated (unless otherwise stated), but rather to provide a general view of the memory accessible by the computer system 100 and how such is used.

As shown in FIG. 1B, the processor 105 includes a number of functional modules including a control unit 139, an arithmetic logic unit (ALU) 140, and a local or internal memory 148, sometimes called a cache memory. The cache memory 148 typically includes a number of storage registers 144-146 in a register section. One or more internal busses 141 functionally interconnect these functional modules. The processor 105 typically also has one or more interfaces 142 for communicating with external devices via the system bus 104, using a connection 118. The memory 134 is coupled to the bus 104 using a connection 119.

The application program 133 includes a sequence of instructions 131 that may include conditional branch and loop instructions. The program 133 may also include data 132 which is used in execution of the program 133. The instructions 131 and the data 132 are stored in memory locations 128, 129, 130 and 135, 136, 137, respectively. Depending upon the relative size of the instructions 131 and the memory locations 128-130, a particular instruction may be stored in a single memory location as depicted by the instruction shown in the memory location 130. Alternately, an instruction may be segmented into a number of parts each of which is stored in a separate memory location, as depicted by the instruction segments shown in the memory locations 128 and 129.

In general, the processor 105 is given a set of instructions which are executed therein. The processor 105 waits for a subsequent input, to which the processor 105 reacts to by executing another set of instructions. Each input may be provided from one or more of a number of sources, including data generated by one or more of the input devices 102, 103, data received from an external source 173, e.g., a medical imaging device 173 such as an MRI or DTI scanner, X-ray, ultrasound or other medical imaging device across one of the networks 120, 122, data retrieved from one of the storage devices 106, 109 or data retrieved from a storage medium 125 inserted into the corresponding reader 112, all depicted in FIG. 1A. The execution of a set of the instructions may in some cases result in output of data. Execution may also involve storing data or variables to the memory 134.

Some techniques described in this specification use input variables 154, e.g., data sets characterizing one or more anatomical or surgical structures, which are stored in the memory 134 in corresponding memory locations 155, 156, 157. The techniques can produce output variables 161, which are stored in the memory 134 in corresponding memory locations 162, 163, 164. Intermediate variables 158 may be stored in memory locations 159, 160, 166 and 167.

Referring to the processor 105 of FIG. 1B, the registers 144, 145, 146, the arithmetic logic unit (ALU) 140, and the control unit 139 work together to perform sequences of micro-operations needed to perform "fetch, decode, and execute" cycles for every instruction in the instruction set making up the program 133. Each fetch, decode, and execute cycle can include i) a fetch operation, which fetches or reads an instruction 131 from a memory location 128, 129, 130; ii) a decode operation in which the control unit 139 determines which instruction has been fetched; and iii) an execute operation in which the control unit 139 and/or the ALU 140 execute the instruction.

Thereafter, a further fetch, decode, and execute cycle for the next instruction may be executed. Similarly, a store cycle may be performed by which the control unit 139 stores or writes a value to a memory location 132.

Each step or sub-process in the techniques described in this specification may be associated with one or more segments of the program 133 and is performed by the register section 144, 145, 146, the ALU 140, and the control unit 139 in the processor 105 working together to perform the fetch, decode, and execute cycles for every instruction in the instruction set for the noted segments of the program 133. Although a cloud-based platform has been described for practicing the techniques described in this specification, other platform configurations can also be used. Furthermore, other hardware/software configurations and distributions can also be used for practicing the techniques described in this specification.

Figure 2:
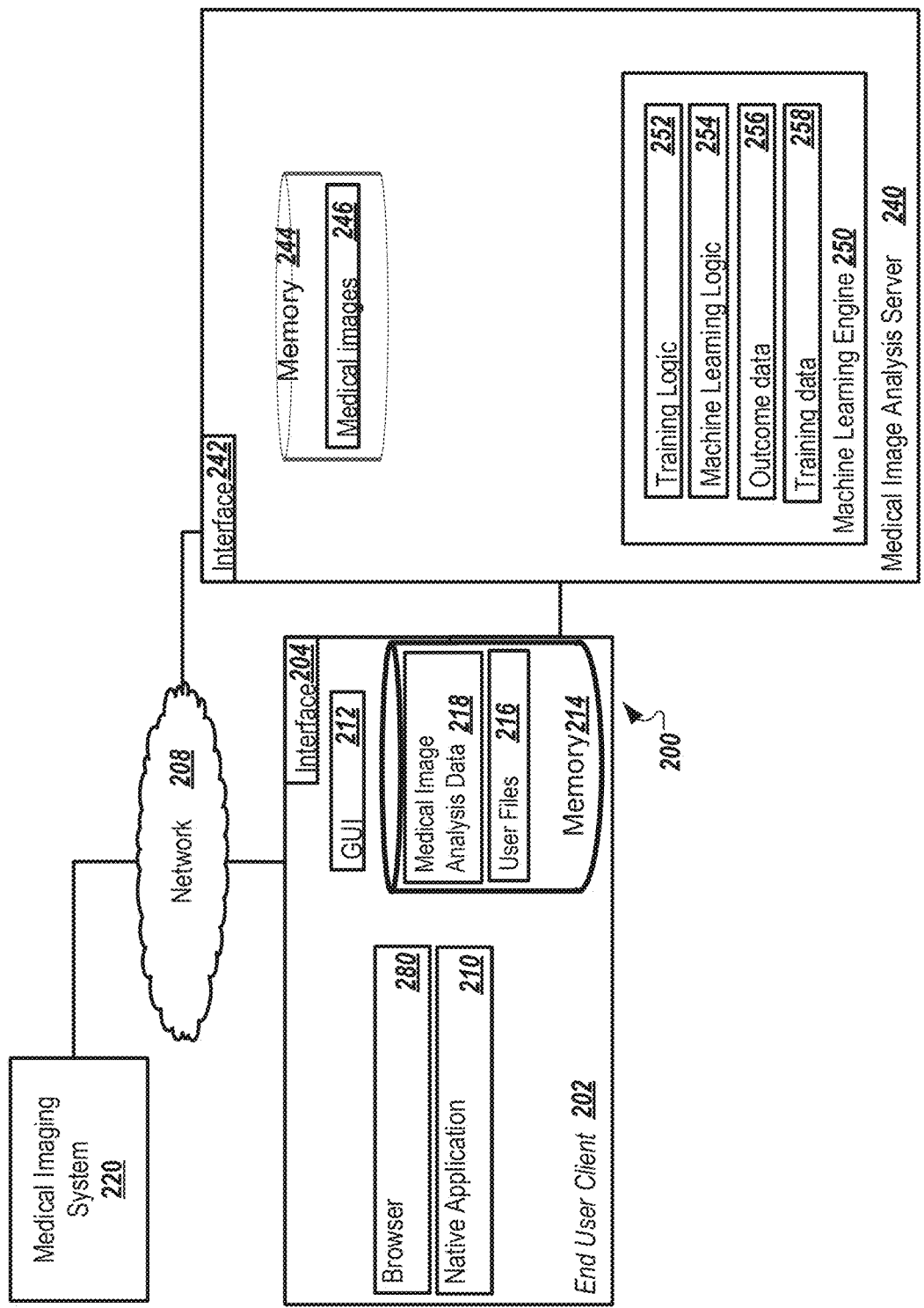
FIG. 2 is a block diagram of an example system for mapping brain data to behavior.

FIG. 2 is a block diagram illustrating an example system 200 for mapping brain data to behavior. The system of FIG. 2 may be implemented within a computer system as described with reference to FIGS. 1A and 1B. Specifically, the illustrated system 200 includes or is communicably coupled with a Medical Image Analysis server 240, an end-user client device 202, a network 208 (which can include a local area network (LAN), a wide area network (WAN), the Internet, or a combination thereof), and a medical imaging system 220. Although shown separately, in some implementations, functionality of two or more systems, devices, or servers may be provided by a single system or server. In some implementations, the functionality of one illustrated system, server, or engine may be provided by multiple systems, servers, or engines, respectively.

An end-user client device 202 (also referred to herein as client device 202 or device 202) is an electronic device that is capable of requesting and receiving content over the network 208. The end-user client device 202 can include any client computing device such as a laptop/notebook computer, wireless data port, smart phone, personal data assistant (PDA), tablet computing device, one or more processors within these devices, or any other suitable processing device that can send and receive data over the network 208. For example, the end-user client device 202 can include, e.g., a computer that includes an input device, such as a keypad, touch screen, or other device that can accept user information, and an output device that conveys information, e.g., associated with the operation of the Medical Image Analysis server 240, or the client device itself, including digital data, visual information, or the GUI 212. The end-user client device 202 can include one or more client applications (as described above). A client application is any type of application that allows the end-user client device 202 to request and view content on a respective client device. In some implementations, a client application can use parameters, metadata, and other information received at launch to access a particular set of data from the Medical Image Analysis server 240. In some instances, a client application may be an agent or client-side version of the one or more enterprise applications running on an enterprise server (not shown).

The end-user client device 202 typically includes one or more applications, such as a browser 280 or a native application 210, to facilitate sending and receiving of content over the network 108. Examples of content presented at a client device 202 include images from medical imaging system 220.

Medical imaging system 220 can be any appropriate imaging system, for example an MRI system, CT system, X-ray system, ultrasound system etc. In an implementation, the medical imaging system may be a functional MRI (fMRI) imaging, for example resting state fMRI images of the brain. In other examples the imaging data may selected from at least one of, Magnetoencephalograph (MEG), electroencephalograph (EEG), magnetic resonance imaging (MRI), diffusion tensor imaging (DTI). While only one medical imaging system 220 is shown in FIG. 2 images can be received from one or more medical imaging systems.

As described further with reference to FIGS. 3 and 4, an end user, of the end-user client device 202 may desire to use a machine learning engine 250 located at Medical Image Analysis server 240 to carry out one or more tasks associated with analyzing one or more medical images. For example, the user may use a machine learning engine 250 to process one or more images generated by medical imaging system 220. In an implementation the medical images may be associated with one or more sets of symptoms. To do that, the end user of the client device 202 can provide data to the Medical Image Analysis server 240. The end user client device 202 provides this interface for display via its graphical user interface (GUI) 212.

On this interface, the end user can provide input. The user input can include for example one or more selections of a series of medical images 246, e.g. fMRI images to make a measurement of an anatomical structure or functional properties, for example a fMRI image processed to show a connectomic map of the brain of a subject or subjects suffering from or displaying a particular set of symptoms or behaviors. In another embodiment the series of images may be selected automatically by machine learning engine 250. Once the end user enters and submits this information on the interface, machine learning engine 250 of the Medical Image Analysis server 240 processes this data to determine a likelihood 252 that particular data derived from a brain activity sensing system, e.g., a connectivity matrix derived from the medical images 246, is associated with a particular behavior or symptom. A connectivity matrix reveals the strength of connections between different brain regions, e.g., between different regions or volumes of the brain, which are known as parcels. In one embodiment, there can be hundreds of parcels, e.g., 379 parcels resulting in tens of thousands of unique matrix elements (e.g., more than 70,000 unique matrix elements).

Machine learning engine 250 can include training logic 252 used to train machine learning logic 254 to identify one or more behaviors or symptoms associated with particular structures or variables in the series of medical images. Training of machine learning logic, e.g. machine learning logic 254 is described in more detail below with reference to FIG. 7. Machine learning engine 250 can further include machine learning logic 254. Machine learning logic 254 can be any appropriate machine learning algorithm. For example, some appropriate machine learning algorithms are linear regression, logistic regression, Bayes classifiers, random classifiers, decision trees, neural networks. In a particular example, described herein with reference to FIG. 4, the machine learning logic 254 is a boosted decision tree. Outcome data 256 may be associated with training data 258 in order to train the machine learning logic 254 to identify functional data, e.g., connectivity data, associated with particular symptoms or behaviors. Connectivity data can take the form of a connectivity matrix. A connectivity matrix can be a matrix where the value in an element of the matrix represents the degree of correlation of activity between the parcels (e.g., parcellations) represented by the column and row of the element.

In some implementations, the end user of the client device 202 can store the received Medical Image Analysis data 218 in the client device 202's memory 214 (along with other user files 216 that may already be stored in the memory 214).

Memory 214 and memory 244 included in the end-user client device 202, may each include any memory or database module and may take the form of volatile or non-volatile memory including, without limitation, magnetic media, optical media, random access memory (RAM), read-only memory (ROM), removable media, or any other suitable local or remote memory component.

Figure 3A:
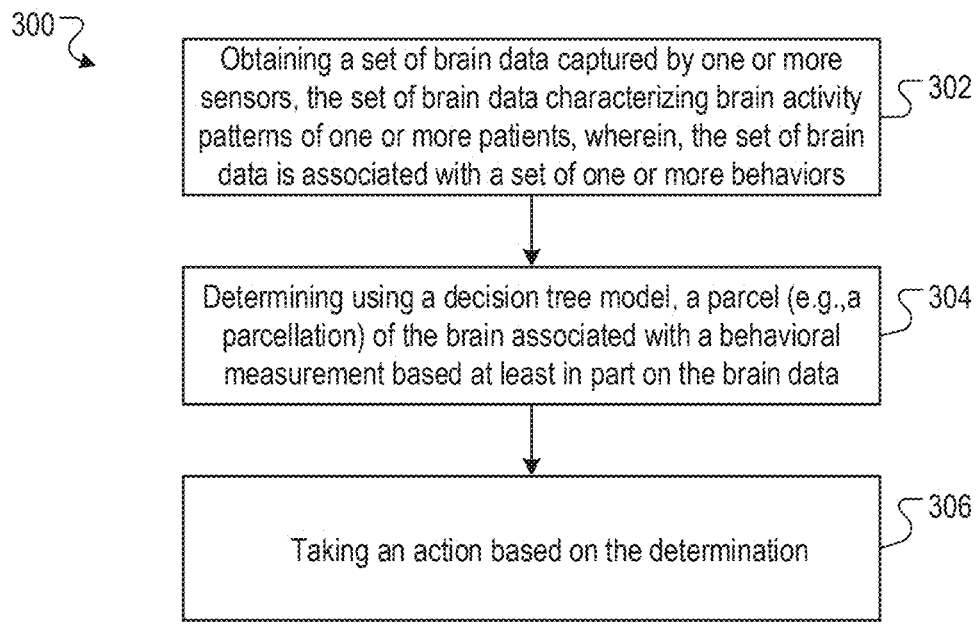
FIG. 3A is a flow diagram of an example process for using machine learning to map connectomic data to behavior.

FIG. 3A is a flow diagram of an example process 300 for using machine learning to map connectomic data to behavior.

The process 300 can include obtaining 302 a set of brain data captured by one or more sensors, the set of brain data characterizing brain activity patterns of one or more patients, wherein, the set of brain data can be tagged with a quantified set of one or more behaviors, e.g., by a clinician observing the patient and/or by categorizing a subject's writings and/or audio and/or video recordings of a subject. The brain data may be obtained using one or more medical imaging modalities, e.g., Magnetoencephalograph (MEG), electroencephalograph (EEG), magnetic resonance imaging (MRI), diffusion tensor imaging (DTI), or functional MM imaging (fMRI). For example the data may can be resting state fMRI data. The data can be processed to generate an input connectivity matrix, for example using fMRI data to capture the brain's network activity (either at rest or while performing directed tasks), enabling the identification of distinct areas of the brain that are functionally connected.

A decision tree model, for example a trained boosted decision tree model, can be used to determine 304 a degree of a behavior based at least in part on the brain data. For example, the trained decision tree model can be used to assess whether a specific set of activations found in a connectomic matrix is correlated with a specific clinical/behavioral observation. For example, whether an activation corresponds to a degree of a behavior on the Positive and Negative Syndrome Scale (PANSS), a medical scale used for measuring symptom severity of patients with schizophrenia. Other examples can include whether an activation corresponds to a level of specific behaviors or attributes (e.g., a level of literacy), or other mental or physical symptoms.

In an implementation, resting state fMRI data can be used to generate a connectivity matrix with various activations. The decision tree model e.g. boosted decision tree can be used to assess how various activations are associated with symptom severity. For example, one symptom measured using the PANSS scale is conceptual disorganization which indicates a level of disordered thinking, with 1 being mild and 7 being extreme. The level of severity of conceptual disorganization (or other mental or physical symptoms) can be predicted based on various activations in the fMRI or other connectomic matrix data using a trained boosted decision tree model. Predicting the severity of symptoms using a boosted decision tree model is further described herein with reference to FIGS. 4-7.

An action 304 can be taken based on the degree of the behavior predicted by the boosted decision tree model. For example, symptoms and their severity can be determined using the boosted decision tree model, this enables more accurate management of disease and it's progression. For example, such an action could include changing a medication dose, predicting a likely response to treatment and adjusting medication in a preemptive manner, applying transcranial magnetic stimulation to the indicated regions/parcels, performing surgery direction to the indicated regions/parcels, and/or performing counseling shown to be effective for the behavior and/or the affected parcels in question.

Figure 3B:
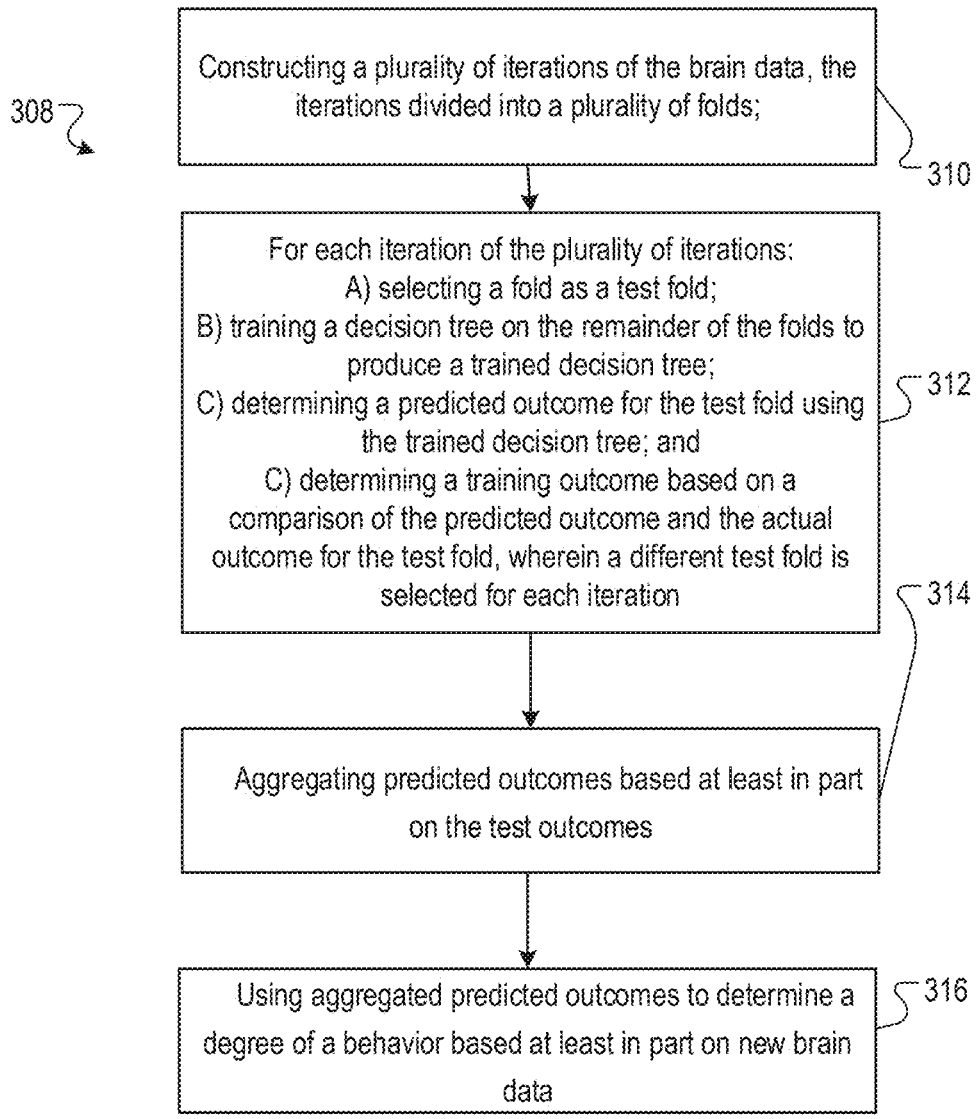
FIG. 3B is a flow diagram of an example process of using aggregated predicted outcomes to determine a degree of a behavior.

FIG. 3B is a flow diagram of an example process 308 of using aggregated predicted outcomes to determine a degree of a behavior. The process includes: A) at step 310 constructing a plurality of iterations of the brain data, the iterations divided into a plurality of folds; B) at step 312, for each iteration of the plurality of iterations: i) selecting a fold as a test fold; ii) training a decision tree on the remainder of the folds to produce a trained decision tree; iii) determining a predicted outcome for the test fold using the trained decision tree; and iv) determining a test outcome based on a comparison of a predicted outcome and an actual outcome for the test fold, wherein a different test fold is selected for each iteration; C) at step 314, aggregating predicted outcomes based at least in part on the test outcomes; and D) at step 316, using the aggregated predicted outcomes to determine a degree of a behavior based at least in part on new brain data, FIG. 4 is an example schematic diagram 400 of a decision tree model, for example a boosted ensemble decision tree. Decision tree models deal well with high dimensional data such as connectomic matrix data since decision tree models facilitate selecting the right depth/split level (e.g. number of variables on which the decision tree splits) and facilitate features of little importance being discarded. This decision tree model approach can be leveraged to "map" an outcome even with small sample set of observations.

In an example, the depth/split level can be user specified based on an assessment of the best value to assess feature importance without over-fitting. In an alternative, the depth/split level can be determined by the machine learning engine 250 using a default value or based on a grid-search of the parameter space.

In another example, a user-selected or automatically determined split can be used for defining feature importance. The resulting tree can be linearized to obtain direction and magnitude of the weights for the features in questions. For example, since each decision is guarded by a feature, and the decision either adds or subtracts from the value given in the parent node, the prediction can be defined as the sum of the feature contributions and the "bias" (i.e. the mean given by the topmost region that covers the entire training set).

The prediction function can be written as $f(x)=C_{full}+\Sigma_{k=1}^{K} contrib(x,k)$ where K is the number of features, $C_{full}$ is the value at the root of the node and contrib(x,k) is the contribution from the k-th feature in the feature vector x. This is superficially similar to linear regression ($f=a+bx$). For linear regression the coefficients b are fixed, with a single constant for every feature that determines the contribution. For the decision tree, the contribution of each feature is not a single predetermined value, but depends on the rest of the feature vector which determines the decision path that traverses the tree and thus the guards/contributions that are passed along the way. The prediction of a plurality of decision trees (e.g. a forest) can be made using an average or aggregate of the individual tree predictions to achieve a result over all members of the forest. The random forest is therefore more interpretable. In some examples a level of interpretability similar to linear models can be achieved.

With reference again to FIG. 4 providing a schematic view of an example of a decision tree 400, the decision tree includes a root node 402 guarded by feature RM and having a trained mean value of 22.60. If one follows path 404, e.g., if RM<=6.94, one comes to node 406 guarded by feature LSAT and having a value of 19.96 (thus the path experienced a loss of 2.64 (the loss from RM=19.96−22.60). If one continues to follow path 404, e.g., if LSAT<=14.40, then one arrives at node 408 guarded by feature DIS with a value of 23.47 (thus the path 406 experienced a gain of 3.51 (the gain from LSTAT=23.47−19.96). If one continues to follow path 404, e.g., if DIS<=1.38, then one arrives at node 410 with a value of 45.59 (thus the path 406 experienced a gain of 22.12 (the gain from DIS=45.59−23.47). In sum, the prediction from this tree for traversing path 404 is 45.59 which comes from 22.60 (trained mean)−2.64 (loss from RM)+3.52 (gain from LSTAT)+22.12 (gain from DIS).

Boosted decision tree ensembles can include a sequence of consecutive trees, at each level. The trees can be trained in a consecutive way. Each individual model can learn from mistakes made by the previous model. In such a consecutive approach, when an input is misclassified by a hypothesis, its weight is increased so that next hypothesis is more likely to classify it correctly. Combining the whole set at the end converts weak learners into a better performing model. Any appropriate method of boosting may be used, for example gradient boosting, XGboost, ADAboost, random forest etc. In an example, when dealing with small samples, Synthetic Minority Over-sampling Technique (SMOTE) can be used to artificially balance the sample and create minority class (low respondent) observations.

FIG. 5 is a schematic diagram of an example decision table 500 for a subject which shows for each feature in a connectomic matrix (shown in feature column 502) its importance when predicting the severity of a behavior or symptom of interest. The level of importance can be given by the absolute weight 504, the value 506 and/or rank weight 508 of each feature. The decision tree is shown as an example only, depending on the correlation of brain parcel (e.g. area of the brain) to the behavior/symptom/response being investigated. Table 1 shows examples of variables that can be used by an ML algorithm to obtain a ranged ranking of a brain parcels

TABLE 1

| Variable | Definition |
| --- | --- |
| Feature | Feature as fed to the ML algorithm |
| Weight | Importance associated with feature |
| Value | Measured value associated with feature |
| Feature_0 | First item of a pair in the feature |
| Feature_1 | Second item of a pair in the feature |
| Abs_weight | Absolute (weight) |
| Rank weight | Rank order of weight |
| Prod | Weight*value |
| Abs_prod | Absolute(prod) |
| Rank_prod | Rank order of product |

Figure 6:
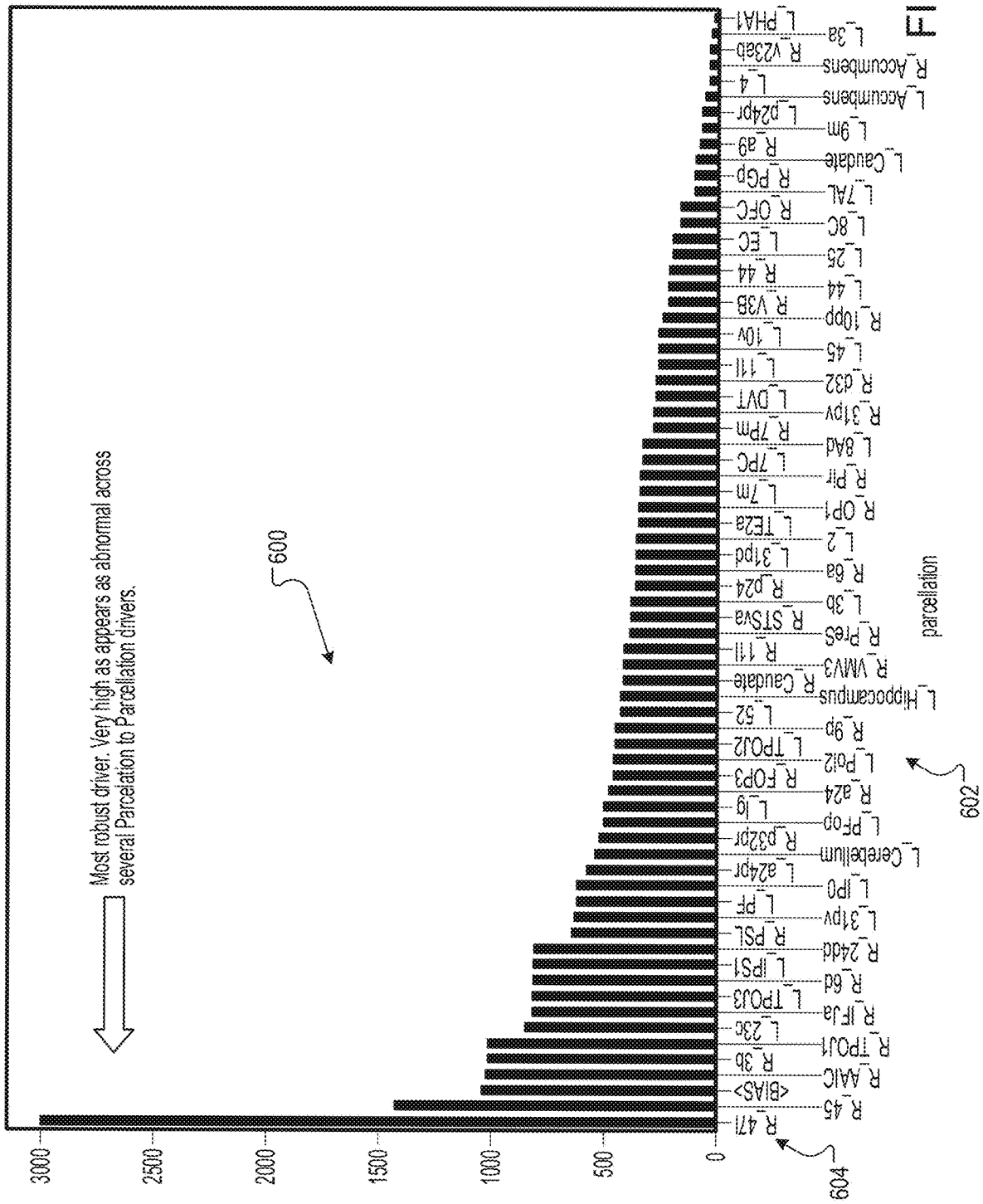
FIG. 6 is a schematic diagram of an example outcome of a machine learning process.

FIG. 6 is a schematic diagram of an example outcome 600 of a machine learning process. In the example shown in FIG. 6 a plurality of features 602 are plotted against their likelihood of contributing to a behavior or symptom. For example, if the behavior is conceptual disorganization, as described above, the features plotted can be the likelihood of a particular feature in the connectomic matrix (e.g., a parcel such as a parcellation) contributing to a PANSS score of 2 for conceptual disorganization. The level of contribution of each feature can be based on a score output from the boosted decision tree ensemble. For example the score can be calculated as a sum of Rank (abs(weight)*value). It can be seen that in the described example one feature (feature R471) 604 appears to be a particularly robust driver of a particular degree of a behavior.

Figure 7:
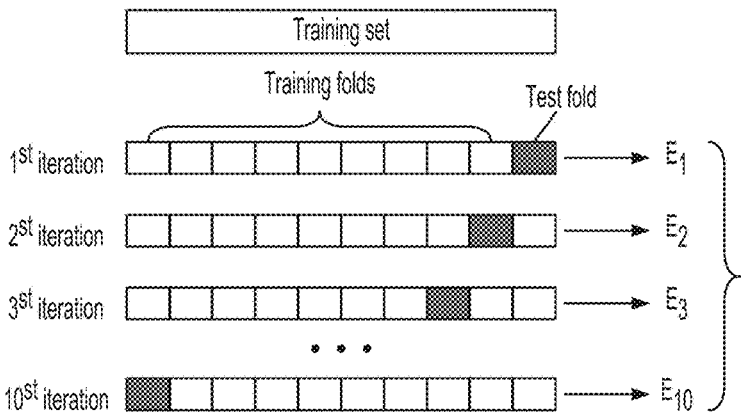
FIG. 7 is a schematic diagram of an example means of performing a cross-validation process.

In some examples, particularly when the data set is small, it can be difficult to stabilize feature importance across different runs, i.e. to consistently predict which features are strong drivers of particular behaviors or symptoms. Decision tree models can often be unstable with small variations in the training set resulting in different trees and different predictions for the same validation examples, that is, running a model trained on a first training data set might lead to a different feature importance than a model trained on a second training data set. This is particularly true when training data sets are small. One mechanism for improving the robustness of the model is shown in FIG. 7. FIG. 7 is a schematic diagram of an example means of performing a cross-validation process. The data set 700, for example, the set of brain data as described above is divided into a plurality of folds 702, e.g. a plurality of groups of data. For example, each fold can be the brain image date of a particular person. In a first iteration 708 a first fold 704 is selected as a test fold. The remainder of the folds 706 are used as training folds and used to train the boosted decision tree ensemble model, an example of which is shown in FIG. 4. In one example, the data may include brain data associated with a plurality of individuals, and the system selects an individual's brain data as a test fold and the rest of the data related to other individuals is used as a training set. The system can iterate through each individual, i.e., the system can iterate by selecting a different individual's brain data as the test fold for each iteration until many, most, or all of the individuals" brain data has served as the test fold in an iteration. In another example the data could be, for example, brain data associated with the same individual take at different times. Again the system can iterate through folds of data (in this case folds comprising an individual's brain data taken at different times) to produce a set of resulting models. An ensemble model can be derived by processing (e.g. averaging) the set of resulting models.

The outcome of the boosted decision tree ensemble trained using the training folds is a trained model that is used to try to predict the outcome(s) in the test fold. As noted above, the data set can be iterated through with each fold of the plurality of folds iteratively selected as a test fold and the decision tree model trained on the remainder of the folds. For each iteration (708-714) a training outcome and a test outcome can be received and the training and test outcomes aggregated across all iterations. The aggregated test outcomes 716 can be used to determine which features in the brain data (e.g. connectomic matrix) contribute to a particular degree or severity of a symptom.

Area Under the Curve (AUC) can be used to create a mapping between features (connectivity matrices) and outcome (measured behavior). AUC provides an aggregate measure of performance across all possible classification thresholds. The aim is not necessarily to create a high AUC model, rather a mapping can be achieved with each run of the algorithm at which point feature importance is extracted. The feature importance is averaged over several runs therefore reinforcing the signal over noise.

In one implementation, for a given quantified behavior/trait, for which a small sample of data is available (e.g., 50 individual with that trait and 50 without it), and for which rsFMRI data is available,
  a. A tree based model is fitted to predict the presence or absence of that trait.
  b. The importance of features (i.e., how much a specific activation correlation between two parcelations) as to a specific prediction are extracted/determined.
  c. The feature importance values are combined into a decision table.
  d. Metrics are derived from that decision table, e.g., feature values and their respective weights are multiplied to derive subject specific importance values.
  e. The specific importance is ranked per subjects to allow cross subject comparison.
  f. Ranks are combined to derive the global importance of each feature.
  g. The aggregated ranking is used to show for a tree based model, on a limited sample size, which feature is more contributive to the prediction of the outcome.
  h. Other ways to work with the decision can also be used, such as measuring the directionality of the importance, the magnitude of the importance.

An alternative to running a single cross-validation experiment and aggregating test outcomes is a method that performs hyper-parameter tuning to improve the AUC of the model, and then uses a single top performing model to determine which features in the brain data contributed most to prediction of the symptom. The steps involved can be the following:
  performing hyper-parameter tuning by considering a few key parameters of the model, and doing a grid search over a range of values for each of these parameters;
  For each new combination of parameters, performing cross validation to assess the AUC;
  Once the method determines the optimal set of parameters (that produce the highest AUC), using these parameters to train a new model over the entire dataset (no cross validation required);
  then taking this single (top performing) model and using the same Hollow-tree Super (HoTS) method to determine which features in the brain contributed most to the prediction of a symptom.

An advantage of this approach is that the method will be applying the HoTS method to a better performing model which is more likely to make correct predictions. This alternative method also doesn't have to aggregate test results.

In some implementations this procedure can be carried out for brain data from a plurality of patients and each combination of brain activity data and degree of a behavior/trait can be ranked for a particular patient based at least in part on the weight indicative of the strength of cross validation. In an example ranking for all patients can be aggregated to provide an indication of a strength of the cross-validation i.e. the likelihood that a particular feature is likely to be a driver of a degree or severity of a symptom or behavior across a broad population.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method comprising:
obtaining a set of brain data captured by one or more sensors, the set of brain data characterizing brain activity patterns of a patient;
processing the set of brain data to produce processed brain data;
for each of a plurality of parcel pairs, determining, using a trained model and based at least in part on the processed brain data, the importance of an activation correlation between a pair of parcels of the brain to predicting a behavioral measurement, the trained model trained using a set of training brain data characterized with a behavior expression metric scored on a standardized scale, wherein determining the importance of an activation correlation comprises determining a weight and an activation correlation value of the parcel pair;
repeating for each of a plurality of parcels,
for each of the plurality of parcel pairs that include a specified parcel from the plurality of parcels, determining a value of a function of the weight and the activation correlation value of the parcel pair, and determining the importance of the specified parcel to the behavioral measurement based on the sum of the values of the function for each of the plurality of parcel pairs including the specified parcel, wherein repeating for each of the plurality of parcels provides individual parcel data for individual parcels that contribute to the behavioral measurement,
wherein the determining the importance of a parcel comprises applying the processed brain data to a linearized tree model to determine magnitude and direction of a contribution of the parcel to the behavior and wherein a contribution of the parcel depends on a feature vector which determines a decision path that traverses the linearized tree model;
forwarding, for display to a user, the individual parcel data of individual parcels where the individual parcels are not provided in the context of a parcel pair; and
taking an action based on the determination of the magnitude and direction of the contribution of the parcel to the behavior.

2. The method of claim 1 wherein the linearized tree model is an ensemble tree model.

3. The method of claim 1 wherein the brain data is selected from at least one of, Magnetoencephalograph (MEG), electroencephalograph (EEG), magnetic resonance imaging (MRI), diffusion tensor imaging (DTI), near-infrared spectroscopy (NIRS) or functional MRI imaging (fMRI).

4. The method of claim 1 wherein the brain data is resting state fMRI data.

5. The method of claim 2 wherein determining a parcel of the brain associated with a behavioral measurement comprises:
performing cross-validation of the linearized tree model; and,
applying a weight to each combination of brain activity pattern and degree of behavior, the weight indicative of an importance of that brain activity pattern for predicting the degree of behavior or presence of symptom.

6. The method of claim 5, wherein performing cross-validation comprises:
constructing a plurality of iterations of the brain data, the iterations divided into a plurality of folds;
for each iteration of the plurality of iterations:
selecting a fold as a test fold;
training a decision tree on the folds remaining to produce a trained decision tree;
determining a predicted outcome for the test fold using the trained decision tree; and
determining a test outcome based on a comparison of the predicted outcome and an actual outcome for the test fold, wherein a different test fold is selected for each iteration;
aggregating predicted outcomes based at least in part on the test outcomes; and
using the aggregated predicted outcomes to determine a degree of a behavior based at least in part on new brain data.

7. The method of claim 5 further comprising:
for each patient of one more patients ranking each combination of brain activity data and degree of a behavior based at least in part on the weight indicative of a strength of cross validation.

8. The method of claim 7 further comprising aggregating the ranking for all patients to provide an indication of a strength of the cross-validation.

9. The method of claim 2 wherein determining a parcel of the brain associated with a behavioral measurement comprises:
performing hyper-parameter tuning;
evaluating combinations of parameters with cross-validation;
selecting a combination of parameters that perform above a specified threshold;
applying this set of parameters to a full dataset; and
applying a weight to each combination of brain activity pattern, the weight indicative of the importance of that brain activity pattern for predicting a degree of behavior or presence of symptom.

10. The method according to claim 1 wherein the behavior is a symptom of a disease.

11. The method according to claim 1 wherein the behavior is a response to a treatment.

12. The method according to claim 1 further comprising processing the brain data to produce connectivity matrix data and wherein determining a degree of a behavior comprises determining a degree of a behavior based at least in part on the connectivity matrix data.

13. The method according to claim 1, wherein the behavior is a trait.

14. A system comprising one or more computers and one or more storage devices storing instructions that are operable, when executed by the one or more computers, to cause the one or more computers to perform operations comprising:
  obtaining a set of brain data captured by one or more sensors, the set of brain data characterizing brain activity patterns of a patient, wherein, the set of brain data is associated with a set of one or more behaviors;
  processing the set of brain data to produce processed brain data;
  for each of a plurality of parcel pairs, determining using a trained model and based at least in part on the processed brain data, the importance of an activation correlation between a pair of parcels of the brain to predicting a behavioral measurement, the trained model trained using a set of training brain data characterized with a behavior expression metric scored on a standardized scale, wherein determining the importance of an activation correlation comprises determining a weight and an activation correlation value of the parcel pair;
  repeating for each of a plurality of parcels,
    for each of the plurality of parcel pairs that include a specified parcel from the plurality of parcels, determining a value of a function of the weight and the activation correlation value of the parcel pair, and determining the importance of the specified parcel to the behavioral measurement based on the sum of the values of the function for each of the plurality of parcel pairs including the specified parcel, wherein repeating for each of the plurality of parcels provides individual parcel data for individual parcels that contribute to the behavioral measurement,
  wherein the determining the importance of a parcel comprises applying the processed brain data to a linearized tree model to determine magnitude and direction of a contribution of the parcel to the behavior and wherein a contribution of the parcel depends on a feature vector which determines a decision path that traverses the linearized tree model;
  forwarding, for display to a user, the individual parcel data of individual parcels where the individual parcels are not provided in the context of a parcel pair; and
  taking an action based on the determination of the magnitude and direction of the contribution of the parcel to the behavior.

15. The system of claim 14 wherein the trained decision tree model is an ensemble tree model.

16. The system of claim 15 wherein determining a parcel of the brain associated with a behavioral measurement comprises:
  performing cross-validation of the trained decision tree model; and,
  applying a weight to each combination of brain activity pattern and degree of behavior, the weight indicative of the importance of that brain activity pattern for predicting the degree of behavior or presence of symptom.

17. The system of claim 16, wherein performing cross-validation comprises:
  constructing a plurality of iterations of the brain data, the iterations divided into a plurality of folds;
  for each iteration of the plurality of iterations:
    selecting a fold as a test fold;
    training a decision tree on the remainder of the folds to produce a trained decision tree;
    determining a predicted outcome for the test fold using the trained decision tree; and
    determining a test outcome based on a comparison of a predicted outcome and an actual outcome for the test fold, wherein a different test fold is selected for each iteration;
  aggregating predicted outcomes based at least in part on the test outcomes; and
  using the aggregated predicted outcomes to determine a degree of a behavior based at least in part on new brain data.

18. One or more computer-readable storage media encoded with instructions that, when executed by one or more computers, cause the one or more computers to perform operations comprising:
  obtaining a set of brain data captured by one or more sensors, the set of brain data characterizing brain activity patterns of one or more patients and including first patient brain data characterizing brain activity patterns of a first patient;
  processing the first patient brain data to produce processed first patient brain data;
  for each of a plurality of parcel pairs, determining, using a trained model and based at least in part on the processed brain data, the importance of an activation correlation between a pair of parcels of the brain to predicting a behavioral measurement, the trained model trained using a set of training brain data characterized with a behavior expression metric scored on a standardized scale, wherein determining the importance of an activation correlation comprises determining a weight and an activation correlation value of the parcel pair;
  repeating for each of a plurality of parcels,
    for each of the plurality of parcel pairs that include a specified parcel from the plurality of parcels, determining a value of a function of the weight and the activation correlation value of the parcel pair, and determining the importance of the specified parcel to the behavioral measurement based on the sum of the values of the function for each of the plurality of parcel pairs including the specified parcel, wherein repeating for each of the plurality of parcels provides individual parcel data for individual parcels that contribute to the behavioral measurement,
  wherein the determining the importance of a parcel comprises applying the processed first patient brain data to a linearized tree model to determine magnitude and direction of a contribution of the parcel to the behavior and wherein a contribution of the parcel depends on a feature vector which determines a decision path that traverses the linearized tree model;
  forwarding, for display to a user, the individual parcel data of individual parcels where the individual parcels are not provided in the context of a parcel pair; and
  taking an action based on the determination of the magnitude and direction of the contribution of the parcel to the behavior.

19. The computer-readable storage media of claim 18 wherein the decision model is selected from one of a) a tree model and b) a logistic regression model.

20. The computer-readable storage media of claim 18, wherein the behavior expression metric scored on a standardized scale is scored using the Positive and Negative Syndrome scale.

* * * * *